United States Patent [19]

Soula et al.

[11] 4,094,802
[45] June 13, 1978

[54] NOVEL LUBRICANT ADDITIVES

[75] Inventors: Gerard Soula, Meyzieu; Philippe Duteurtre, Le Havre, both of France

[73] Assignee: Société Orogil, Paris, France

[21] Appl. No.: 782,881

[22] Filed: Mar. 30, 1977

[30] Foreign Application Priority Data

Apr. 1, 1976 France .................. 76 09513

[51] Int. Cl.² .................. C10M 1/32; C10M 3/26; C10M 5/20; C10M 7/30
[52] U.S. Cl. .................. 252/51.5 A; 252/51.5 R; 260/326.26; 260/326.5 F
[58] Field of Search .............. 252/51.5 A; 260/326.26, 260/326.5 F, 51.5 R

[56] References Cited

U.S. PATENT DOCUMENTS

| | | | |
|---|---|---|---|
| 3,018,291 | 1/1962 | Anderson et al. | 260/326.5 F |
| 3,024,237 | 3/1962 | Drummond et al. | 260/326.5 F |
| 3,154,560 | 10/1964 | Osuch | 260/326.26 |
| 3,219,666 | 11/1965 | Norman et al. | 260/268 |
| 3,231,587 | 1/1966 | Rense | 260/346.8 |
| 3,306,907 | 2/1967 | McNinch et al. | 260/326.26 |
| 3,438,899 | 4/1969 | Benoit | 260/326.5 F |

FOREIGN PATENT DOCUMENTS

| | | |
|---|---|---|
| 805,486 | 1/1974 | Belgium. |
| 2,042,558 | 1/1975 | France. |
| 1,356,802 | 6/1974 | United Kingdom. |
| 1,306,529 | 2/1973 | United Kingdom. |

*Primary Examiner*—Helen M. S. Sneed

[57] ABSTRACT

Novel lubricant additives are provided comprising compositions based on alkenylsuccinimides containing at least one alkenylsuccinimide of the formula:

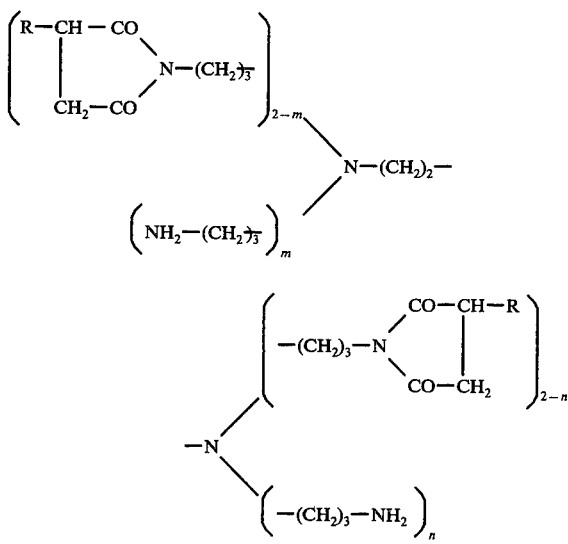

where R is an alkenyl group of about $C_{20}$ to $C_{200}$, $m$ is an integer equal to 0, 1 or 2, and $n$ is an integer equal to 0 or 1. These compositions can be prepared by condensation of an alkenylsuccinic anhydride with N,N,N',N'-tetrakis-(3-aminopropyl)-ethylenediamine.

16 Claims, No Drawings

NOVEL LUBRICANT ADDITIVES

BACKGROUND OF THE INVENTION

The present invention provides novel additive compositions based on alkenylsuccinimides derived from N,N,N',N'-tetrakis-(3-aminopropyl)-ethylenediamine, a novel process for their preparation, and to lubricant products containing the novel additive compositions of the invention.

It is known to react alkenylsuccinic anyhydrides with aliphatic monoamines, aromatic amines, heterocyclic amines and the like, or with alkylidene-polyamines, polyoxyalkylideneamines and the like, and to use the resulting alkenylsuccinimides as additives for lubricants.

By the present invention it has been found that certain novel alkenylsuccinimides of the invention are particularly suitable as detergent/dispersing agent additives, anti-rust additives and anti-foam additives for engine oils.

It is, therefore an object of the present invention to provide a new class of alkenylsuccinimide lubricant additives.

It is also an object of the present invention to provide a novel process for producing lubricant additives.

It is a further object of the present invention to provide novel lubricant compositions comprising a lubricant oil and an additive of the present invention.

Further objects will be apparent to those skilled in the art from the present description.

GENERAL DESCRIPTION OF THE INVENTION

The additive compositions which form a subject of the invention comprise an alkenylsuccinimide of the formula:

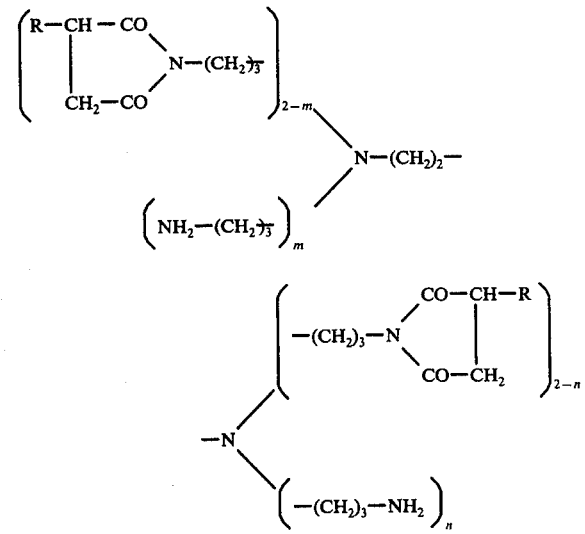

in which formula:

R represents an alkenyl group containing from about 20 to 200 carbon atoms, $m$ represents an integer equal to 0, 1, or 2, and $n$ represents an integer equal to 0 or 1.

The novel additive compositions which form a subject of the invention can be prepared by reaction of an alkenylsuccinic anhydride, in which the alkenyl group contains from about 20 to 200 carbon atoms, with N,N,N',N'-tetrakis-(3-aminopropyl)-ethylenediamine.

The reaction desirably takes place at a temperature of between 120° C. and 230° C., preferably between about 140° C. and 180° C., with a molar ratio of polyamine to alkenylsuccinic anhydride of not more than 1. If appropriate, the reaction is carried out in the presence of a diluent to reduce the viscosity of the reaction mixture; the said diluent will preferably be chosen from among the lubricating oils which can be used as base oils in lubricating compositions, containing the reaction product additive, examples of such base oils being given hereinbelow.

A molar ratio of polyamine to alkenylsuccinic anhydride of 1 and preferably of between about 0.7 and 0.95, makes it possible to obtain additive composition containing a major proportion of monoalkenylsuccinimide. A molar ratio of polyamine to alkenylsuccinic anhydride of between about 0.4 and 0.7 makes it possible to obtain compositions containing a major proportion of bisalkenylsuccinimide. A molar ratio of between about 0.3 and 0.4 makes it possible to obtain compositions containing a major proportion of trisalkenylsuccinimide. A molar ratio of between about 0.25 and 0.3 makes it possible to obtain compositions containing a major proportion of tetrakisalkenylsuccinimide.

The alkenylsuccinic anhydrides employed as a starting material are prepared in a known manner, for example, by thermal condensation (U.S. Pat. No. 3,306,907) of maleic anhydride with a polyolefin of mean molecular weight between about 400 and 4,000. The said polyolefin is chosen from among the oligomers or polymers of optionally branched $C_2$–$C_{30}$ olefins, or the copolymers of the said olefins with one another or with diene or vinyl-aromatic comonomers. Among these polyolefins there may preferentially be mentioned the oligomers of $C_2$–$C_{20}$ α-mono-olefins, such as the oligomers of ethylene, of propylene, of 1-butene, of isobutene, of 3-cyclohexyl-1-butene and of 2-methyl-5propyl-1-hexene, the copolymers of these α-olefins with one another or with internal olefins, and the copolymers of isobutene with a comonomer chosen from among butadiene, styrene, 1,3-hexadiene or conjugated or non-conjugated dienes and trienes.

The condensation reaction to prepare the alkenylsuccinic anhydride material can also be carried out in the presence of chlorine (U.S. Pat. No. 3,231,587 and Belgian Pat. No. 805,486), of iodine (British Pat. No. 1,356,802) or of bromine (French Patent Application No. 74/18915 filed on May 31, 1974 in the name of Rhone-Progil; this corresponds to Soula U.S. Pat. Application Ser. No. 574,720, filed May 31, 1974). This reaction can also be carried out by starting from monochlorinated or monobrominated polyolefins, as is indicated in the French patent published under U.S. Pat. No. 2,042,558.

The N,N,N',N'-tetrakis-(3-aminopropyl)-ethylenediamine starting material can be prepared by cyanoethylation of ethylenediamine with acrylonitrile in a molar ratio of acrylonitrile to amine of about 4, followed by hydrogenation of the nitrile obtained.

A small amount of N,N,N'-tris-(3-aminopropyl)-ethylenediamine can also be present during the reaction of the alkenylsuccinic anhydride with the N,N,N',N'-tetrakis-(3-aminopropyl)-ethylenediamine, without detracting from the performance characteristics of the alkenylsuccinimides obtained.

The present invention also resides in the lubricating oils which have been improved by addition of 1 to 10%, of their weight, of the additive compositions of the invention, described above, which impart their detergent/dispersing, anti-rust, and which impart their detergent/dispersing, anti-rust, and anti-foam properties of the said lubricating oils.

The lubricating oils which can be used can be chosen from among a great variety of lubricating oils, such as lubricating oils based on napthenes, based on paraffins and based on their mixtures, other hydrocarbon lubricants, for example, lubricating oils derived from coal products, and synthetic oils, for example, alkylene polymers, polymers of the alkylene oxide type and their derivatives, including the polymers of an alkylene oxide prepared by polymerizing the alkylene oxide in the presence of water or of alcohols, for example, ethyl alcohol, the esters of dicarboxylic acids, liquid esters of phosphorous acids, alkylbenzenes and dialkylbenzenes, polyphenyls, alkyl biphenyl ethers and silicon polymers.

The amount of new lubricant additives to be added to the lubricating oils depends on the future use of the lubricating oil to be improved; thus, for a gasoline engine oil the amount of lubricant additive to add is desirably from about 1 to 7% by weight; for a diesel engine oil it is from about 4 to 10%.

The improved lubricating oils can also contain antioxidant additives, anti-corrosion additives and the like.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

864 grams of polyisobutenylsuccinic anhydride (PIBSA) of acid number 77.7 (expressed in mg. of potassium hydroxide required to neutralize 1 gram of product), obtained by condensing maleic anhydride with a polyisobutene of molecular weight about 1,000, are introduced into a 2-liter three-necked flask. 96 grams of 100 N oil are added in order to lower this acid number from 77.7 to 70. The resulting mixture is heated at 120° C. while stirring, and 43 grams of tetrakis-aminopropyl-ethylenediamine, corresponding to a molar ratio of polyamine to PIBSA of 0.25, are introduced over the course of 40 minutes. The temperature is raised to 140° C. over the course of 2 hours while gradually reducing the pressure to 20 mm. Hg., and is then kept for 2 hours at 150° C. under 15 mm. Hg.

The product consists predominantly of tetrapolyisobutenyl-succinimide and contains a total nitrogen percentage of 1.2%, and has an acid number of 6.7 mg. of KOH per gram. It has a viscosity of 450 cst at 98.9° C. (210° F.).

The N,N,N',N'-tetrakis-(3-aminopropyl)-ethylenediamine employed to obtain this product can be prepared as described below by cyanoethylation of ethylenediamine with acrylonitrile, followed by hydrogenation of the nitrile obtained.

120.7 g. (2 mols) of ethylenediamine and 200 g. of distilled water are introduced into a 3-liter glass reactor flushed with nitrogen and equipped with a mechanical stirrer, a reflux condenser, a dropping funnel and a thermometer. 636 g. (12 mols) of acrylonitrile are gradually run, over the course of 35 minutes, into the stirred reaction mixture which is kept at a temperature of 25° to 40° C. A limpid slightly yellow solution is obtained, which essentially contains N,N'-bis-(2-cyanoethyl)-ethylenediamine. the solution is then stirred and heated to 70° C. It is kept at a temperature of 70°-76° C. for 40 hours and is then cooled to 20°-25° C. 538 g. of N,N,N',N'-tetrakis-(2-cyanoethyl)-ethylenediamine, in the form of white needles, are thus recovered.

This crude tetranitrile is then purified by recrystallization from absolute ethanol. 507.5 g. of purified product are thus obtained, having a sealed tube melting point of 66.4°-66.8° C.

11 ml. of an aqueous sodium hydroxide solution of 36° Be strength, 400 ml. of a suspension of Raney nickel in absolute ethanol, containing 136 g. of Raney nickel, 544 g. (2 mols) of the tetranitrile obtained above and 544 ml. of ethanol are introduced into a 3.6-liter stainless steel autoclave flushed with nitrogen and equipped with a stirrer system, an injection circuit and a heating and cooling system comprising a waterbath. After closing the autoclave, the latter is flushed three times with nitrogen, then with hydrogen. Hydrogen is then introduced into the autoclave to give a pressure of 40 bars. The autoclave is agitated and heated to a temperature of 35°-40° C., after which it is cooled to 25° C. in 17 minutes. The volume of hydrogen absorbed is 357 liters. The autoclave is then degassed and flushed with nitrogen. The reaction mixture is recovered and the reactor is rinsed with three times 200 ml. of absolute ethanol. The catalyst is filtered off and 2,050 g. of colorless and limpid filtrate are obtained.

12 ml. of hydrochloric acid ($d = 1.19$) are added to the filtrate and the solvent is then distilled by heating to 80° C. under reduced pressure (2 mm. Hg.). 558 g. of a crude residue are obtained, which is filtered to remove the sodium chloride. 546 g. (representing a yield of 88.4%) of a product composed of 95% of N,N,N',N'-tetrakis-(3-aminopropyl)-ethylenediamine and 5% of N,N,N'-tris-(3-aminopropyl)-ethylenediamine, are thus recovered, the product being in the form of a limpid straw-yellow oily liquid.

EXAMPLE 2

1,600 grams, equivalent to 1 mol, of polyisobutenyl-succinic anhydride (PIBSA) of acid number 70 (expressed in mg. of potassium hydroxide required to neutralize 1 gram of product), obtained by condensing maleic anhydride with a polyisobutene of molecular weight about 1,000, are introduced into a 3-liter three-necked flask. The resulting mixture is heated to 100° C. while stirring. 86 grams of tetrakis-(3aminopropyl)-ethylenediamine, corresponding to a molar ratio of polyamine to PIBSA equal to 0.3, are introduced over the course of 30 minutes. The temperature is raised to 140° C. over the course of 2 hours while gradually reducing the pressure to 25 mm. Hg. and is then brought for 1 hour to 150° C. under 25 mm. Hg.

The product obtained consists predominantly of tris-polyisobutenyl-succinimide and contains a total nitrogen percentage of 1.45% and has an acid number of 3.6 mg. of KOH per gram. It has a viscosity of 590 cst at 98.9° C. (210° F.).

EXAMPLE 3

350 grams of polyisobutenylsuccinic annhydride (PIBSA) of acid number 80 (expressed in mg. of potassium required to neutralize 1 gram of product), obtained by condensing maleic anhydride with a polyisobutene of molecular weight about 1,000 are introduced into a 1-liter three-necked flask. 50 grams of 100 N oil are added as a diluent. The resulting mixture is heated to 110° C. while stirring. 24 grams of tetrakis-(2-aminopropyl)-ethylenediamine, corresponding to a molar ratio of polyamine to PIBSA of 0.33, are introduced in the course of 10 minutes. The temperature is raised to 140° C. over the course of 3 hours while gradually reducing the pressure to 25 mm. Hg.

The product obtained is a mixture of tetra- and tris-polyisobutenylsuccinimide and contains a nitrogen percentage 1.62% and has an acid number of 4.5 mg. of KOH per gram.

EXAMPLE 4

1,600 grams of polyisobutenylsuccinic anhydride (PIBSA) of acid number 70 (expressed in mg. of potassium hydroxide required to neutralize 1 gram of product), obtained by condensing maleic anhydride with a polyisobutene of molecular weight about 1,000, are introduced into a 3-liter three-necked flask. The resulting mixture is heated to 100° C. while stirring. 36 grams of tetrakis)-3-aminopropyl)-ethylenediamine, corresponding to a molar ratio of polyamine to PIBSA equal to 0.5, are introduced over the course of 15 minutes. The temperature is raised to 140° C. while gradually reducing the pressure to 25 mm. Hg. These conditions are maintained for 3 hours. the product obtained consists predominantly of bis-polyisobutenylsuccinimide and contains a nitrogen percentage of 2.24% and has an acid number of 11.3 mg. of KOH per gram.

EXAMPLE 5

1,600 grams, equivalent to 1 mol, of polyisobutenyl-succinic anhydride (PIBSA) of acid number 70 (expressed in mg. of potassium hydroxide required to neutralize 1 gram of product), obtained by condensing maleic anhydride with a polyisobutene of molecular weight about 1,000, are introduced into a 3-liter three necked flask. The mixture is heated to 100° C. while stirring. 230 grams of tetrakis-(3-aminopropyl)-ethylenediamine, corresponding to a molar ratio of polyamine to PIBSA equal to 0.8, are introduced over the course of 30 minutes. The temperature is raised to 140° C. over the course of 2 hours while gradually reducing the pressure to 25 mm. Hg. and is then brought for 1 hour to 150° C. under 25 mm. Hg.

The product obtained consists predominantly of monopolyisobutenylsuccinimide and contains a total nitrogen percentage of 3.7% and has an acid number of 2 mg. of KOH per gram.

EXAMPLE 6

1,400 grams of polyisobutenylsuccinic anhydride (PIBSA) of acid number 80 (expressed in mg. of potassium hydroxide required to neutralize 1 gram of product), obtained by condensing maleic anhydride with a polyisobutene of molecular weight about 1,300 are introduced into a 2-liter three-necked flask. 200 grams of 100 N oil are added in order to bring this number from 80 to 70. The resulting mixture is heated to 130° C. while stirring and 72 grams of tetrakis-[aminopropyl]-ethylenediamine, corresponding to a molar ratio of polyamine to PIBSA of 0.25, are introduced over the course of 40 minutes. The temperature is raised to 140° C. over the course of 2 hours while gradually reducing the pressure to 20 mm. Hg. and is then brought for 2 hours to 150° C. under 15 mm. Hg.

the product obtained consists predominantly of tetrapolyisobutenyl-succinimide and contains a total nitrogen percentage of 1.3% and has an acid number of 5.3 mg. of KOH per gram.

EXAMPLE 7

The products of the invention obtained in accordance with the above examples were tested from the point of view of their dispersing properties in lubricants. The dispersing power was studied in accordance with the spot method described in Volume 1 of the work by A. Schilling, "Les huiles pour moteur et le graissage des moteurs" ("Engine oils and engine greasing oils") 1962 edition, pages 89–90.

The method is carried out on 20 grams of SAE 30 oil to which are added 5 grams of sludge coming from an $AV_1$ Petter engine and containing about 2% of carbonaceous matter.

The SAE 30 oil has beforehand been modified by adding the following formulation (the amounts of the various additives being given per kilogram of oil): 50 mols of dispersing agent additive of each Examples 1 to 6 to be studied, 30 mmols of calcium alkylbenzenesulphonate, 30 mmols of calcium alkylphenate containing excess alkali and 15 mmols of zinc dihexyldithiophosphate.

The mixture of additive-modified oil and sludge is separated into 5 fractions which are stirred and subjected to the following 5 heat treatments:

(1) a fraction subjected to heating at 50° C. for 10 minutes;

(2) a fraction subjected to heating at 200° C. for 10 minutes;

(3) a fraction subjected to heating at 250° C. for 10 minutes;

(4) a fraction subjected to heating at 50° C. for 10 minutes in the presence of 1% of water;

(5) a fraction subjected to heating at 200° C. for 10 minutes in the presence of 1% of water.

A drop of each mixture obtained after the heat treatment is deposited on a filter paper.

The rating is made after 48 hours. For each spot, the percentage of product dispersed relative to the spot of oil is calculated by determining the ratio of the respective diameters of the spot of oil and of the dispersed product. The higher the percentage of dispersed product, the better the dispersing action on the sludge.

The ratings shown in Table I below are thus obtained.

EXAMPLE 8

The anti-rust properties of the products of Examples 1 to 6 are tested in SAE 30 oil modified by the addition of the formulation of the preceding example, namely, per 1 kg. of oil: 50 mmols of one of the products of Examples 1 to 6; 30 mmols of calcium alkylbenzenesulphonate; 30 mmols of calcium alkylphenate containing excess alkali and 15 mmols of zinc dihexyldithiophosphate.

The principle of the test consists of adding, to the oil to be studied, the products which may be present in the blow-by gases and which play a role in the formation of rust on the combination of valve-pusher and valve-stem, and of immersing a piece which forms part of the said combination into the mixture thus obtained, for a certain time. The rust formed is rated visually.

The test is carried out by introducing 700 grams of oil into a flask and heating to 50° C. while stirring, successively adding, when the temperature has stabilized, 20 cm.³ of a 30% strength aqueous formaldehyde solution, 4.5 cm.³ of methanol, 5 cm.³ of a 50/50 mixture of dichloroethane and dibromoethane, and 8.5 cm.³ of a 78.5% strength aqueous solution of nitric acid, and immersing a piece of the combination of valve-pusher and valve-stem for 19 hours in the mixture.

If there is no attack, the product is given a rating of 20; if the attack is very extensive, it is given a rating of 0. The rating results are shown in Table 1, below.

EXAMPLE 9

The anti-foam properties of the products of Examples 1 to 6 are measured in accordance with Standard Specification ASTM D 892.63, in SAE 30 oil modified by addition of the formulation indicated in Examples 7 and 8.

The rating results are shown in Table 1, below.

Comparison Test

Comparable tests of each of Examples 7, 8 and 9 are carried out by replacing the products of Examples 1 to 6 by the same amount of a prior art succinimide (Product "A"), namely, bis-(polyisobutenylsuccinimide) derived from triethylene-tetramine and from a PIBSA of acid number 74 obtained by condensing maleic anhydride and a polyisobutene of molecular weight about 1,000.

The results of these tests are also shown in the Table below.

TABLE 1

| | Performances | | |
|---|---|---|---|
| Product | Dispersion (Test of Example 7) | Anti-rust (Test of Example 8) | Anti-foam (Test of Example 9) |
| Additive of | | | |
| Example 1 | 450 | 12 | 10 - traces |
| 2 | 440 | 14 | 10 - traces |
| 3 | 420 | 12 | 10 - traces |
| 4 | 400 | 10 | 10 - traces |
| 5 | 400 | 10 | 10 - traces |
| 6 | 460 | 13 | 10 - traces |
| Product"A" | 380 | 11.5 | 600 - 450 |

It is found that the best results obtained correspond to a molar ratio of diamine to PIBSA of less than about 0.5.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. What is claimed is:

1. A novel additive composition based on alkenylsuccinimides, comprising an alkenylsuccinimide of the formula (I):

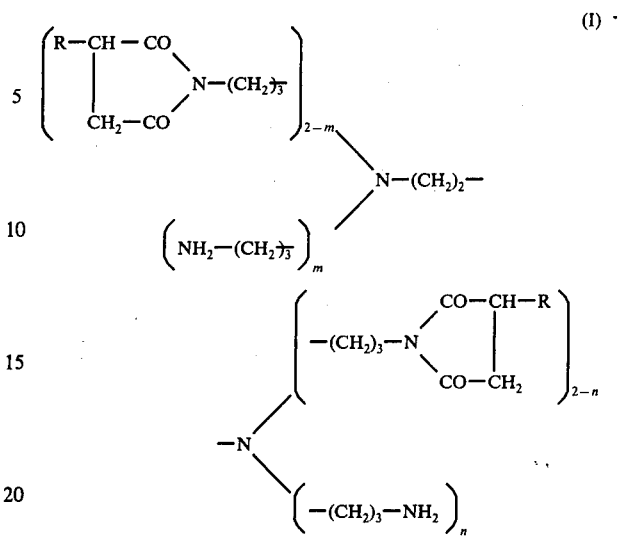

in which formula R represents an alkenyl group containing from about 20 to 200 carbon atoms, $m$ represents an integer selected from the group consisting of zero, 1 and 2, and $n$ represents an integer selected from the group of zero and 1.

2. A novel additive composition according to claim 1, wherein the alkenylsuccinimide of the formula I is a tetraalkenylsuccinimide.

3. A novel additive composition according to claim 1, wherein the alkenylsuccinimide of the formula I is a trisalkenylsuccinimide.

4. A novel additive composition according to claim 1, wherein the alkenylsuccinimide of the formula I is a bisalkenylsuccinimide.

5. A novel additive composition according to claim 1, wherein the alkenylsuccinimide of the formula I is a monoalkenylsuccinimide.

6. A novel additive composition according to claim 1, wherein the radical "R" in formula I represents a polyisobutenyl group containing from about 20 to 200 carbon atoms.

7. A novel additive composition according to claim 2, wherein the radical "R" in formula I represents a polyisobutenyl group containing from about 20 to 200 carbon atoms.

8. A novel additive composition according to claim 3, wherein the radical "R" in formula I represents a polyisobutenyl group containing from about 20 to 200 carbon atoms.

9. A novel additive composition according to claim 4, wherein the radical "R" in formula I represents a polyisobutenyl group containing from about 20 to 200 carbon atoms.

10. A novel additive composition according to claim 5, wherein the radical "R" in formula I represents a polyisobutenyl group containing from about 20 to 200 atoms.

11. A lubricating composition having desirable dispersion, anti-rust and anti-foam properties, comprising an oil containing between about 1 and 10% by weight of a novel additive according to claim 1.

12. A lubricating composition having desirable dispersion, anti-rust and anti-foam properties, comprising an oil containing between about 1 and 10% by weight of a novel additive according to claim 2.

13. A lubricating composition having desirable dispersion, anti-rust and anti-foam properties, comprising an oil containing between about 1 and 10% by weight of a novel additive according to claim 3.

14. A lubricating composition having desirable dispersion, anti-rust and anti-foam properties, comprising an oil containing between about 1 and 10% by weight of a novel additive according to claim 4.

15. A lubricating composition having desirable dispersion, anti-rust and anti-foam properties, comprising an oil containing between about 1 and 10% by weight of a novel additive according to claim 5.

16. A lubricating composition having desirable dispersion, anti-rust and anti-foam properties, comprising an oil containing between about 1 and 10% by weight of a novel additive according to claim 6.

* * * * *

UNITED STATES PATENT AND TRADEMARK OFFICE
CERTIFICATE OF CORRECTION

PATENT NO. : 4,094,802
DATED : June 13, 1978
INVENTOR(S) : Gerard Soula et al.

It is certified that error appears in the above–identified patent and that said Letters Patent are hereby corrected as shown below:

Col. 1, line 12, delete "anyhydrides" and replace with
-- anhydrides --.

Col. 2, line 16, delete "composition" and replace with
-- compositions --.

Col. 2, line 39, delete "2-methyl-5propyl-" and replace
with -- 2-methyl-5-propyl- --.

Col. 4, line 57, delete "(3aminopropyl)" and replace
with -- (3-aminopropyl) --.

Col. 5, line 2, delete "annhydride" and replace with
-- anhydride --.

Col. 5, line 29, delete "tetrakis)-3-aminopropyl)" and
replace with -- tetrakis-(3-aminopropyl) --.

Signed and Sealed this

Twenty-fourth Day of October 1978

[SEAL]

Attest:

RUTH C. MASON
Attesting Officer

DONALD W. BANNER
Commissioner of Patents and Trademarks